United States Patent
Mao et al.

(10) Patent No.: US 7,176,008 B2
(45) Date of Patent: Feb. 13, 2007

(54) PROCESS FOR PRODUCING ACTIVATED THROMBIN-ACTIVATABLE FIBRINOLYSIS INHIBITOR

(75) Inventors: Shi-Shan Mao, North Wales, PA (US); Dennis Colussi, Wyndmoor, PA (US); Steve Gardell, Woodbridge, CT (US)

(73) Assignee: Merck & Co., Inc., Rahway, NJ (US)

( * ) Notice: Subject to any disclaimer, the term of this patent is extended or adjusted under 35 U.S.C. 154(b) by 237 days.

(21) Appl. No.: 10/736,793

(22) Filed: Dec. 16, 2003

(65) Prior Publication Data

US 2004/0126815 A1    Jul. 1, 2004

Related U.S. Application Data

(60) Provisional application No. 60/433,727, filed on Dec. 16, 2002.

(51) Int. Cl.
*C12N 9/00* (2006.01)
*A61K 51/00* (2006.01)

(52) U.S. Cl. ..................... 435/183; 424/1.69

(58) Field of Classification Search ................. 435/183
See application file for complete search history.

(56) References Cited

OTHER PUBLICATIONS

Boffa et al., Plasma and recomb. thrombin-activable fibrinol. inhibitor (TAFI) and activatt TAFI comp. with respect to glycosyl., thromb./thrombom..- depend. activ., thermal stability, and enzym. properties. J Biol Chem. Jan. 23, 1998;273(4):2127-35. (InIDS).*
Bajzar et al. Purification and charaterization of TAFI, a thrombin-activable fibrinolysis inhibitor. J. of Biol. Chem., 270(24), pp. 14477-14484, 1995.*
D. Hendricks, et al., J. Clin. Chem. Clin. Biochem. 27, 277-285.
S-S. Mao, et al., J. Biol. Chem. 274, 35046-35052.
W. Wang, et al., J. Biol. Chem. 269, 15937-15944.
D. Hendricks, et al., Biochim. Biophy Acta 1034, 86-92.
M. B. Boffa, et al., J. Biol. Chem. 273, 2127-2135.

* cited by examiner

*Primary Examiner*—Cecilia J. Tsang
*Assistant Examiner*—Maury Audet
(74) *Attorney, Agent, or Firm*—Richard S. Parr; Valerie J. Camara

(57) ABSTRACT

The invention is a process for purifying TAFIa from a serum sample in the presence of a reversible inhibitor of TAFIa. The invention is also a method of measuring the activity of TAFIa in the presence of a reversible inhibitor.

9 Claims, No Drawings

```
SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: chemically synthesized

<400> SEQUENCE: 1

Gly Leu Met Val Gly Gly Val Val Arg
 1               5

<210> SEQ ID NO 2
<211> LENGTH: 8
<212> TYPE: PRT
<213> ORGANISM: Artificial Sequence
<220> FEATURE:
<223> OTHER INFORMATION: chemically synthesized

<400> SEQUENCE: 2

Gly Leu Met Val Gly Gly Val Val
 1               5
```

PROCESS FOR PRODUCING ACTIVATED THROMBIN-ACTIVATABLE FIBRINOLYSIS INHIBITOR

This application claims benefit of Ser. No. 60/433,727, filed Dec. 16, 2002.

BACKGROUND OF THE INVENTION

Carboxypeptidases catalyze the removal of the C-terminal amino acid residues in peptides and proteins. Carboxypeptidases have important biological functions and are widely distributed. Carboxypeptidases are found in the pancreas and digestive tract (carboxypeptidases A and B, CPA and CPB), mast cells (mast cell carboxypeptidase A), the secretory granules of endocrine and neuroendocrine cells (carboxypeptidases E and D, CPE and CPD), plasma cell membrane (carboxypeptidase M, CPM) and the blood (carboxypeptidase N, CPN). Thrombin-Activatable Fibrinolysis Inhibitor (TAFI) is a plasma zymogen of a basic carboxypeptidase. Activated TAFI (TAFIa), also called carboxypeptidase U, plasma carboxypeptidase B and carboxypeptidase R, removes C-terminal Arg or Lys residues.

Removing a C-terminal amino acid may dramatically affect biological functions of peptides and proteins. For example, TAFIa regulates fibrinolysis by removing C-terminal Arg or Lys residues. The fibrinolytic cascade is the physiological pathway for plasmin activation and fibrin degradation. Partially degraded fibrin contains C-terminal basic residues that accelerate fibrinolysis by providing binding sites for tissue plasminogen activator (tPA), plasminogen and plasmin. Exposed C-terminal lysine residues of partially degraded fibrin plays a key cofactor role by accelerating the rate of plasmin activation by two to three orders of magnitude. Thus, TAFIa curtails fibrinolysis by removing C-terminal lysine residues. TAFIa inhibitors would therefore be beneficial in the treatment of thrombosis.

TAFIa is unstable at physiological temperature and activity quickly diminishes during serum preparation. Hendriks, D., Scharpe, S., van Sabde, M, and Lommaert, M. P. (1989), *J. Clin. Chem. Clin. Biochem.* 27, 277–285. TAFIa shows a half-life of 74 min at 25° C. Mao, S-S., Cooper, C. M., Wood, T., Shafer, J. A. and Gardell, S. J. (1999), *J. Biol. Chem.* 274, 35046–35052. Although TAFIa is more stable at lower temperature, attempts to efficiently isolate TAFIa at low temperatures were unsuccessful, with <1% activity yield. Wang, W. Hendriks, D. F. and Scharpe, S. S. (1994), *J. Biol. Chem.* 269, 15937–15944; Hendriks, D., Wang, W., Scharpe, S., Lommaert, M-P., van Savde, M. (1990), *Biochim. Biophy. Acta* 1034, 86–92. Reversible TAFIa inhibitors such as ε-aminocaproic acid, when added to TAFIa in vitro, have been reported to preserve stability. However, stable TAFIa has not been formed and purified in the presence of a reversible TAFIa inhibitor. Boffa, M. B., Wang, W., Bazjar, L., and Nesheim, M. E. (1998), *J. Biol. Chem.* 273, 2127–2135;

The present invention provides stable purified activated TAFI, and a method of purifying stable activated TAFI from serum.

The invention also provides more efficient and sensitive assays for carboxypeptidase activity.

SUMMARY OF THE INVENTION

The invention is a process for purifying TAFIa from a serum sample comprising a) adding a reversible inhibitor of TAFIa to the serum sample to form a first mixture; b) adding a coagulation initiator to the first mixture to convert TAFI to TAFIa and form a second mixture; c) applying the second mixture to a heparin-sepharose column to bind TAFI and TAFIa to the column; d) washing the heparin-sepharose column to remove proteins not bound to the heparin-sepharose column; e) eluting the bound TAFI and bound TAFIa from the heparin-sepharose column to form a third mixture; f) applying the third mixture to a TAFIa isolation column to bind TAFIa to the isolation column; g) washing the TAFIa isolation column to remove proteins not bound to the TAFIa isolation column; and h) eluting the bound TAFIa from the TAFIa isolation column.

The invention is also a method of measuring the activity of TAFIa in the presence of a reversible inhibitor comprising: a) contacting a peptide, comprising a C-terminal carboxylate moiety masked by an amino acid, with TAFIa, in the presence of a reversible inhibitor of TAFIa, to form a first mixture; b) unmasking the C-terminal carboxylate moiety by hydrolyzing the amino acid with TAFIa; c) adding a labeled antibody or other labeled protein, which recognizes the unmasked C-terminal carboxylate moiety on the peptide, to the first mixture, to form a second mixture; and d) measuring the extent of hydrolysis by determining the amount of labeled antibody or other labeled protein bound to the unmasked C-terminal carboxylate moiety on the peptide of the second mixture.

The foregoing general description and the following detailed description are exemplary and are intended to provide further explanation of the claimed invention.

DETAILED DESCRIPTION OF THE INVENTION

Coagulation initiators induce the coagulation response that converts TAFI to TAFIa. These initiators include, but are not limited to, calcium chloride, thrombin, and thrombomodulin.

The TAFIa isolation column further isolates TAFIa, and can be, for example, a potato carboxypeptidase inhibitor affinity column or concanavalin A column, or other chromatography column including hydrophobic and chelating interaction.

Reversible inhibitors are compounds which inhibit carboxypeptidase activity by about 70% or greater. Such inhibitors include, but are not limited to, ε-aminocaproic acid, 2-mercaptomethyl-3-guanidinoethyl-propanoic acid, potato tuber carboxypeptidase inhibitor, leech carboxypeptidase inhibitor, or tomato carboxypeptidase inhibitor. Preferably, the reversible inhibitor is ε-aminocaproic acid.

The peptide used in the method for measuring TAFIa activity may be GLMVGGVVR-COOH (SEQ. ID NO. 1), including an N-terminal biotin moiety, although other peptides may be employed.

Antibody or other protein includes a G2-10 antibody, see Rogers, M. V. (1997) Drug Discovery Today 2, 156–160, labeled, for example, with Ruthenium.

Amino acid masking the C-terminal carboxylate moiety is one for which the carboxypeptidase to be measured is selective. For TAFIa, the amino acid can be arginine.

The procedure described above for masking TAFIa activity can be used to measure activity of the basic carboxypeptidases selective for particular amino acids such as arginine or lysine, including carboxypeptidase B, carboxypeptidase N, carboxypeptidase M, carboxypeptidase E, and carboxypeptidase Z.

Some abbreviations that may appear in this application are as follows:

| ABBREVIATIONS | |
|---|---|
| Designation | |
| AlphaScreen | Amplified Luminescent Proximity Homogeneous Assay Screen |
| BSA | bovine serum albumin |
| CON-A | Concanavalin A |
| CP | carboxypeptidase |
| EACA | ε-aminocaproic acid, (also referred as 6-aminocaproic acid) |
| ECL | electrochemiluminescence |
| FA-AR | 3-(2-furyl)acryloyl-L-Ala-L-Arg |
| FFRCK | D-Phe-L-Phe-L-Arginyl chloromethyl ketone |
| FPRCK | D-Phe-L-Pro-L-Arginyl chloromethyl ketone |
| GEMSA | 2-guanidinoethylmercaptosuccinic acid |
| HTRF | homogeneous time-resolved fluorescence |
| PCI | potato carboxypeptidase inhibitor |
| PEG | polyethylene glycol |
| Plummer's Inhibitor | DL-2-mercaptomethyl-3-guinidinoethylthiopropanoic acid |
| TAFI | thrombin-activatable fibrinolysis inhibitor |
| TAFIa | activated thrombin-activatable fibrinolysis inhibitor |
| TM | thrombomodulin |

The inventive method of purifying TAFIa comprises adding a reversible inhibitor of choice, such as ε-aminocaproic acid, during the serum preparation, and keeping the reversible inhibitor present while isolating TAFIa.

EXAMPLE 1

Purification of TAFIa from Human Serum

Step 1

Pooled human plasma (30–40 mL) was diluted 10-fold with HBE buffer (10 mM HEPES, pH 7.4, 5 mM ε-aminocaproic acid). 5 mM of the reversible inhibitor ε-aminocaproic acid was added to maintain TAFIa stability during the isolation.

Thrombin, thrombomodulin and calcium chloride (final concentrations 5 nM, 2 nM and 5 mM, respectively) were added and the solution was shaken at room temperature for 30 min. The formation of serum was quenched with 10 μM FPRCK and centrifuged at 20,000×g for 30 min at 4° C. Unless otherwise mentioned, all isolation steps were performed at 4° C. The fibrin-free solution was loaded onto a heparin-sepharose column (2.5×3 cm) pre-equilibrated with HBE buffer.

In the presence of 5 mM ε-aminocaproic acid, TAFIa activity in serum reached a maximum at ~5 min and was preserved >30 min at 37° C. Initial studies for formation of serum by simply adding thrombin and calcium only activated a limited amount of TAFI zymogen (<<0.5%) as determined with western blotting. Dilution of the plasma for serum preparation increased TAFI activation. A 4–5-fold increase in TAFI activation was observed if the plasma were diluted 10–20-fold. Serum preparation at room temperature for 30 min showed similar activation. The presence of thrombomodulin significantly increased TAFIa generation in a dose-dependent manner. A maximal increase (30–35-fold) was obtained with 2 nM thrombomodulin, consistent with the fact that thrombomodulin is the cofactor for thrombin-mediated TAFI activation. The influence of the intrinsic and extrinsic pathway for TAFI activation was studied using factor VIII- and VII-deficient plasma, respectively. Factor VII-deficient plasma showed a similar level of TAFI activation to normal plasma while factor VIII-deficient plasma exhibited a 3-fold reduction of TAFI activity. These results suggest that the feedback activation of thrombin from the intrinsic pathway is important for TAFI activation in serum.

Step 2

To retain the activity of TAFIa from serum, a reversible inhibitor, such as for illustration and not limitation ε-aminocaproic acid, was added to the serum preparation and ε-aminocaproic acid was kept present while isolating TAFIa. TAFIa activity was then maintained at 4° C. for more than 3 days.

TAFIa as well as its zymogen can bind to heparin. Mao, S-S., Cooper, C. M., Wood, T., Shafer, J. A. and Gardell, S. J. (1999), *J. Biol. Chem.* 274, 35046–35052. A heparin affinity chromatography column was used to initially isolate and quickly remove the majority of proteins including serum albumin, which co-migrated using an anion-exchange column. Carboxypeptidase N (CPN) activity was also removed during chromatography on the heparin affinity column. Increasing the NaCl concentration to 150 mM prior to loading the sample onto the heparin column markedly accelerated the washout time of other proteins from 20–30 min to 2 hr. A linear gradient of 0.15 to 1 M NaCl caused slightly earlier elution of the protein peak (~0.3 M NaCl) than fractions containing TAFIa activity (~0.42 M NaCl). To accelerate isolation, batch elution with a buffer containing 1 M NaCl was applied to obtain smaller pool volumes for loading onto the potato carboxypeptidase inhibitor-affinity column. Recovery of 70–100% of TAFIa activity was typical.

The heparin-sepharose column was washed with HBE buffer containing 150 mM NaCl until absorbance at 280 nm was <0.1. Enzyme activity was then eluted with HB buffer with 1 M NaCl and 5-mL fractions were collected. The pooled solution was dialyzed against HBE buffer with 150 mM NaCl. The dialyzed solution was slowly loaded (~0.2 mL/min) onto a potato carboxypeptidase inhibitor-sepharose column (1.5×3 cm) for more than 3 hr. The column was washed with HBE buffer with 1 M NaCl until $A_{280nm}$<0.02, then further washed with HBE buffer with 0.5% tween 20 (~5 column volumes). TAFIa activity was eluted with a carbonate buffered solution containing 100 mM $NaHCO_3$ (pH 11), 100 mM NaCl and 0.5% Tween-20. Each fraction was neutralized with 1/7.5-volume of neutralization buffer containing 1 M HEPES, pH 7.0, 100 mM NaCl, and 0.1% PEG-8000. Fractions with TAFIa activity were pooled and dialyzed against HBE buffer. For further concentration, the potato carboxypeptidase inhibitor pooled solution was loaded onto a heparin column (1 mL) and eluted with HBE with 1 M NaCl.

Following isolating by heparin-sepharose column, TAFIa is further isolated with a potato carboxypeptidase inhibitor affinity column or a CONCANAVALIN A column.

An affinity chromatography column with potato carboxypeptidase inhibitor, a potent, selective TAFIa inhibitor, was used to isolate pure TAFIa. Concentration of the heparin pooled solution prior to loading resulted in a loss of activity. By slowly loading (~0.2 mL/min) the pooled solution, >40% of activity was retained. TAFIa could not be eluted using a carbonate buffer (pH 11) with high salt (0.5–2 M NaCl) as used successfully to isolate CPA and CPB. Ager S. P. & Hass G. M. (1977), *Anal. Biochem.* 83, 285–295. By adding Tween-20 (0.5%) in the carbonate buffer, TAFIa was eluted from the potato carboxypeptidase inhibitor column. The overall recovery of activity with both heparin and affinity chromatographies was 12–14%.

Alternatively, and in contrast to the low recovery with potato carboxypeptidase inhibitor affinity chromatography, a Concanavalin A column was used to isolate TAFIa with recovery of ~50–70% of the activity. TAFIa isolated using concanavalin A chromatography was suitable for inhibition studies when compared with potato carboxypeptidase inhibitor-affinity-purified TAFIa or the zymogen-activated enzyme.

TAFIa activity was measured with 50 nM electrochemiluminescence substrate after diluted with HBSP buffer (50 mM HEPES, pH 7.4, 150 mM NaCl 0.1% PEG 8000) at room temperature.

Preparation of the heparin-sepharose column was modified from the procedures previously reported. March, S. C., Patrikh, I., and Cuatrecasasm, P. (1974) *Anal. Chem.* 60, 149–152. Twenty grams of heparin (from Sigma, grade I-A from porcine intestine mucosa) were dissolved in 20 mL of 200 mM $NaHCO_3$, pH 9.5, and dialyzed in 3500 MWCO dialysis tubing (Spectra/Por 7 from Spectrum Medical Industries, Los Angeles, Calif.) against 4 L of 200 mM $NaHCO_3$ with four buffer changes at 4° C. Sepharose 4B (500 mL) was washed with 2 L of 100 mM NaOAc (pH 4.0) with 1 M NaCl, rinsed with 2 L of water, then washed with 2 L of 100 mM NaOH. This washing sequence was repeated once. The washed sepharose gel was finally rinsed with water and suspended in 500 mL cold water and diluted with 1 L of cold 2 M $Na_2CO_3$. Fifty grams of cyanogen bromide (Sigma-Aldrich) were dissolved in 25 mL acetonitrile and added to the sepharose slurry with stirring in an ice bath for 4 min. The mixture was quickly filtered, washed with 500 mL of 200 mM $NaHCO_3$, pH 9.5, and then transferred to the dialyzed heparin solution. The coupling mixture was shaken for 3 hr at room temperature, then overnight in a cold room. The mixture was filtered, washed with deionized water, and the slurry was stirred briefly in 1.5 L of 100 mM ethanolamine, pH 8.0. The mixture was filtered, washed with 100 mM NaOAc/1 M NaCl (pH 4.0), rinsed with water and then washed with 100 mM $NaHCO_3$/1 M NaOH (pH 10). The final heparin-sepharose was stored at 4° C. in HEPES-buffered saline containing 50 mM HEPES, pH 7.5, 100 mM NaCl with 0.02% $NaN_3$.

Potato carboxypeptidase-Sepharose was prepared in a manner similar to the preparation of heparin-sepharose preparation. Washing could regenerate the potato carboxypeptidase inhibitor-sepharose with 6 M guanidine hydrochloride in 100 mM tris buffer, pH 7.5. Ager S. P. & Hass G. M. (1977) *Anal. Biochem.* 83, 285–295. Rabbit lung thrombomodulin and human plasminogen were purchased from Hematologic Technologies, Inc. (Essex Junction, Vt.). Recombinant tissue plasminogen activator (t-PA, Alteplase-Activase) with a specific activity of 580,000 IU/mg was from Genentech, Inc (South San Francisco, Calif.). Thrombin was from Enzyme Research Laboratories (South Bend, Ind.). Human carboxypeptidase A, human carboxypeptidase B (CPB) and human carboxypeptidase N (CPN) were purchased from Elastin Product Co. (Owensville, Mo.). Human soluble carboxypeptidase M (CPM) was obtained from Dr. Randal Skidgel (University of Illinois at Chicago). Human soluble carboxypeptidase E (CPE) and carboxypeptidase Z (CPZ) were from Dr. Lloyd Fricker (Albert Einstein College of Medicine).

Pooled human normal plasma, Factors VII- and VIII-deficient plasma and immuno-depleted Protein C plasma were from George King Biomedical, Inc. (Overland Park, Kans.). Potato carboxypeptidase inhibitor, ε-aminocaproic acid, polyethylene glycols (PEG) 20,000 and 8,000, phenyl-methyl sulfonyl fluoride, and aprotinin were purchased from Sigma (St. Louis, Mo.). The concentration of potato carboxypeptidase inhibitor was determined by absorbance at 280 nm with an extinction coefficient of 12.7 $mM^{-1}cm^{-1}$. 3-(2-Furyl)-acryloyl-Alanine-Arginine (FA-AR) was purchased from Bachem (King of Prussia, Pa.). The concentration of FA-AR (dissolved in deionized water) was determined by absorbance at 304 nm using an extinction coefficient of 2.3 $mM^{-1}cm^{-1}$. Neutravidin was from Pierce (Rockford, Ill.). Bovine serum albumin (fraction V) (BSA), D-Phe-L-Pro-L-Arginyl chloromethyl ketone (FPRCK), and D-Phe-L-Phe-L-Arginyl chloromethyl ketone (FFRCK) were purchased from Calbiochem (La Jolla, Calif.). Triton X-100, dimethyl sulfoxide (DMSO) and benzamidine were from Fisher Scientific (Fair Lawn, N.J.). Tween-20 was from Bio-Rad Laboratories (Hercules, Calif.).

Plummer's Inhibitor (DL-2-mercaptomethyl-3-guinidino-ethylthiopropanoic acid), and 2-guanidinoethylmercapto-succinic acid (GEMSA) were from Calbiochem (San Diego, Calif.). Protamine sulfate (grade X from salmon, $M_r$ 5,000) was from Sigma and dissolved in 6 N HCl (10 mg/ml). Synthetic electrochemiluminescence substrate (Biotinyl-EACA-EACA-Gly-Leu-Met-Val-Gly-Gly-Val-Val-Arg-OH) (SEQ. ID NO. 1)) and product (Biotinyl-EACA-EACA-Gly-Leu-Met-Val-Gly-Gly-Val-Val-OH) (SEQ. ID NO. 2)) were prepared by Midwest Bio-Tech Inc. (Fisher, Ind.). Concentrations of the electrochemiluminescence substrate and product peptide were determined using quantitative amino acid analysis. Monoclonal antibody G2-10 was from Cymbus Biotechnology Limited (Chandlers Ford, UK). Origen TAG-NHS ester was from Igen, Inc. (Gaithersburg, Md.). Sepharose 4B, lysine-sepharose, Con A-sepharose, phenyl-sepharose were obtained from Amersham Bioscience. (Piscataway, N.J.).

EXAMPLE 2

Purification of TAFIa from Non-human Serum

Mouse TAFIa was purified using the same protocol of human TAFIa. Mouse plasma was treated with thrombin, thrombomodulin and calcium chloride. Mouse TAFIa was then purified using the heparin column, followed by a Con-A column.

Activated TAFI levels in non-human plasma were also determined by the electrochemiluminescence assay. Activated TAFI zymogen level in animal plasma were obtained as follows: Pooled human, rhesus monkey, African green monkey, dog and rat plasma (50–100 μL) were diluted 20-fold with HB buffer containing 5 mM ε-aminocaproic acid. Thrombin, thrombomodulin and calcium chloride (final concentration 5 nM, 2 nM, and 5 mM, respectively) were added to trigger clot formation for 30 min at room temperature. The reaction was quenched with FPRCK (final concentration 10 μM). The activity of TAFIa was measured using the electrochemiluminescence assay after a series of dilutions (1:20 to 1:200).

Activation of TAFI in diluted plasma samples was initiated with thrombin, thrombomodulin and $CaCl_2$ in the presence of ε-aminocaproic acid for 30 min at room temperature. Plasma samples were diluted and TAFIa activity was measured using the electrochemiluminescence assay.

Higher TAFIa activity (10–30 fold) was observed in mouse and rat serum than in primate serum. Adding thrombomodulin increased TAFIa level in all species. All species showed a saturated effect of thrombomodulin at 2 nM. Enhancement was an order of magnitude in human and African green monkey in the presence of thrombomodulin.

However, slight enhancements (~2-fold) were observed in dog, rat, and mouse in the presence of thrombomodulin The assay for measuring basic carboxypeptidase activity involves use of a C-terminal recognizing antibody to detect carboxypeptidase activity of a carboxypeptidase selective for a particular amino acid, when the carboxypeptidase uncovers a masked C-terminal carboxylate moiety on a peptide substrate masked by the particular amino acid, by hydrolyzing the particular amino acid. The method of measuring carboxypeptidase activity comprises revealing a C-terminal carboxylic acid moiety on a peptide substrate which is blocked by an amino acid, such as arginine, by hydrolysis by a carboxypeptidase selective for that amino acid, and adding an antibody which recognizes and binds to the now revealed C-terminal carboxylic acid moiety on the peptide.

A peptide substrate containing a C-terminal arginine blocking the carboxylate group is hydrolyzed by adding the basic carboxypeptidase, such as TAFIa. After the carboxypeptidase hydrolyzes the amino acid, an antibody that recognizes and binds to the newly exposed C-terminal carboxylic acid on the peptide, such as G2-10, is added. For detection, the antibody may be labeled, e.g., with Ruthenium. The substrate peptide may also contain an N-terminal biotin for coupling to streptavidin. The hydrolyzed peptide product with an N-terminal biotin group binds both streptavidin-coated magnetic beads and labeled antibody. The amount of peptide product is then determined by analyzing the sample in a series M8 Analyzer (Igen). By substituting with other amino acids at the C-terminus, carboxypeptidase activity of other carboxypeptidases selective for those other amino acids can be detected. The assay can be expanded to detection techniques other than electrochemiluminescence, such as HTRF and AlphaScreen for high throughput screening of candidate drugs.

The interactions of several commercial inhibitors with low concentrations of carboxypeptidases were determined using the carboxypeptidase activity assay. The assay allowed determination of the level of activatable thrombin-activated fibrinolysis inhibitor in human and animal plasma in the presence of several inhibitors, such as ε-aminocaproic acid, an active-site inhibitor that stabilizes activated TAFI. A biphasic time course of TAFI activation was observed during the clot lysis process with the two phases likely due to activation by thrombin and plasmin during the coagulation and fibrinolysis pathway, respectively.

The electrochemiluminescence assay was used to evaluate enzyme activity during the new method of purifying stable TAFIa from human serum by applying an active site reversible inhibitor, e.g., ε-aminocaproic acid. Furthermore, using the assay and TAFIa-stabilizing ε-aminocaproic acid, TAFIa levels in different species and kinetics of TAFI activation during the clot formation-lysis process were measured.

EXAMPLE 3

Electrochemiluminescence Assays of Basic carboxypeptidase Activity

A typical assay (75 μL) contained each studied carboxypeptidase and selected inhibitors (in 5 μL DMSO) in HBSP buffer in 96-well round bottom microtiter plates (Costar 3365 plates). Enzyme and compound were preincubated for 15–30 minutes at room temperature. The reaction was initiated by addition of the Biotinylated peptide substrate (Biotinyl-EACA-EACA-Gly-Leu-Met-Val-Gly-Gly-Val-Val-Arg-OH (SEQ. ID NO. 1)) in HBSP buffer. The final substrate concentration was 15 to 50 nM. The amount of carboxypeptidase activity was titrated to result in 40,000–50,000 electrochemiluminescence counts (typically 0.02–0.1 nM, 0.01 nM, 5 nM, and 0.15–0.65 nM. for TAFIa, CPB, CPN and CPM, respectively). Reactions proceeded for 30 min (TAFIa and CPB) or 3 hr (CPM and CPN) at room temperature and were quenched by adding 25 μL of either 0.8 μM potato carboxypeptidase inhibitor (TAFIa and CPB) or 20 μM Plummer's Inhibitor (CPN and CPM). Ruthenium-labeled G2-10 (25 μL of 0.063 μg/mL) and streptavidin magnetic beads (25 μL of 0.2 mg/mL, Dynabeads M-280) were added to the quenched solution and shaken at 300 rpm for >1 hr. G2-10 antibody and beads were prepared in a BSA diluent containing 150 mM phosphate, pH 7.8, 150 mM NaCl, 3% (w/v) BSA (protease free fraction V) and 0.05% NaN$_3$. The volume was brought to 250 μL with HBSP and read on an Igen 96-well electrochemiluminescence plate reader (M8 Analyzer) at 620 nm. Subtraction of background activity in solutions containing only substrate was performed to determine the final activity. Standard curves of product turnover were established using synthetic product peptide (Biotinyl-EACA-EACA-Gly-Leu-Met-Val-Gly-Gly-Val-Val-OH (SEQ. ID NO. 2)). One unit was defined as one nM product generated per min.

Ruthenium-labeled G2-10 monoclonal antibody was prepared with slight modifications from the manufacturer's protocol (Igen). Adding TEG-NHS ester in DMSO to a G2-10 solution (1.5–2 mg/ml) in commercial phosphate-buffered saline, pH 7.8 triggered coupling. The ratio of antibody to TEG reagent was optimal at 1:15. The reaction solution was wrapped with aluminum foil, and shaken for 1 hr at room temperature. The reaction was quenched with 2 M glycine (40 μL/mL reaction mixture) and mixed for an additional 20 min. The quenched solution was then applied to a G-25 PD-10 sizing column (10 mL, Amersham Bioscience) equilibrated with phosphate-buffered saline containing 0.02% NaN$_3$. Ruthenium-labeled G2-10 was eluted with the same buffer, and the yellow fractions were collected. The concentration of the labeled antibody was determined using a commercial kit (Biorad) with purified bovine serum albumin as the standard (Pierce).

This antibody recognition assay was used to examine the activity of several basic carboxypeptidases. The activity of CPB, TAFIa, CPN, CPM, CPE and CPZ was determined using the electrochemiluminescence assay, with a range of sensitivities. TAFIa and CPB activity could be detected with the highest sensitivity, on the order of 1–2 pM of enzyme. CPN and CPZ showed the lowest sensitivity, with $k_{cat}/K_m$ of 100–1000 M$^{-1}$ s$^{-1}$. Changing the C-terminal amino acid to lysine may increase the turnover in CPN- and CPZ-catalyzed reactions. In addition, G2-10 antibody could be substituted with PDZ domains that also recognize C-terminal carboxylic acid with various sequences. Hung, A. Y. and Sheng, M. (2002), *J. Biol. Chem.* 277, 5699–5702; Ferrer, M, Hamilton, A. C. and Inglese, J. (2002), *Anal. Biochem.* 301, 207–216. The electrochemiluminescence assay was used to test a panel of known inhibitors with each of the carboxypeptidases. ε-aminocaproic acid was determined to be a relatively specific inhibitor of CPE activity, with an IC50 of 8 μM, which is >100 fold more potent than its inhibition of CPB. Similarly, protamine was shown to be a specific inhibitor of CPN activity (>100 fold). Both inhibitors are currently used in the clinical setting and their selective inhibition of certain carboxypeptidases may imply potential adverse effects.

Several basic carboxypeptidases were tested at room temperature and at 37° C. Because TAFIa and CPB are relatively unstable, both were studied only at room temperature. Substrate hydrolysis catalyzed by TAFIa was typically quenched at 30 min, but a linear time course was observed for 60 min. With a minimal sensitivity criterion of S/B of 5, CPB had the lowest limit of detection of <1 pM enzyme with 50 nM substrate in a 30 min reaction. Although TAFIa is slightly less active than CPB, a detection limit of <2 pM enzyme was achievable with a short reaction time (30 min). On the other end, CPN and CPZ showed the lowest turnover with this peptide. However, the detection limit of 100 pM still demonstrated good S/B with longer reaction times (4–6 hr). CPM and CPE showed medium activity with a detection limit of <10 pM enzyme at 37° C.

Steady-state kinetics showed different catalytic efficiencies among the enzymes. The catalytic efficiency ($k_{cat}/K_m$) of CPB and TAFIa is three orders of magnitude higher than CPZ and CPN. Values of $K_m$ for TAFIa and CPB were 8 and 12 µM, respectively, and are lower than for the other enzymes. Temperature influenced enzyme activity. Both CPN and CPM exhibited a 2–2.5-fold increase of catalytic efficiency when the temperature was increased. $K_m$ for CPM was 38 µM at room temperature, while the value was much higher (>50 µM) at 37° C. The high $K_m$ values suggest that the substrate concentrations used in the assays, 15–50 nM, are well below $K_m$ for all the enzymes studied which minimizes substrate competition in inhibition studies.

Hydrolysis of substrate by TAFIa, CPB, CPM and CPN was performed in HBSP buffer (pH 7.4). Acetate buffer (pH 5.5) and Tris buffer (pH 7.4) were used for CPE and CPZ, respectively. Studies were conducted at room temperature (~23° C.) or in 37° C. water bath. Product concentrations were measured after dilutions using the electrochemiluminescence assay.

A limitation to the electrochemiluminescence method is that the substrate also binds to the beads, therefore limiting the concentration of substrate that can be used in the assays without diluting the reaction. Because the electrochemiluminescence instrument has a detection limit, the optimal substrate and enzyme concentrations for the assay was titrated. Consistent with the binding capacity of bead and magnet a saturation of the product signal was observed when the substrate concentrations were higher than 100 nM. However, a linear turnover rate was observed with 5–60 nM substrate. The concentrations of enzyme providing about 30,000 to 50,000 electrochemiluminescence units, conditions that showed a signal to background ratio (S/B) of about 40–60, was arbitrarily used.

Inhibition studies of CPE were performed in an acetate buffer containing 125 mM sodium acetate, pH 5.5, 1.25 mM $CoCl_2$ at 37° C. Fricker, L. D. (1995), *Methods in Neurosci.* 23, 237–250. CPE (final concentration 0.15 nM) was pre-incubated with inhibitors for 30 min at room temperature. The electrochemiluminescence substrate (final concentration 50 nM) was added and incubated for 6 hr at 37° C., then quenched with one-third volume of 1 M Tris, pH 8.0. The activity of CPZ was determined in 100 mM Tris, pH 7.4 at 37° C. Novikova, E. G. and Fricker, L. D. (1999), *Biochem. Biophyic. Res. Commun.* 256, 564–568.

CPZ (final concentration 2 nM) was pre-incubated with inhibitors for 30 min at room temperature before substrate was added (final concentration 50 nM). Reactions continued at 37° C. for 6 hr and then were quenched with Plummer's Inhibitor (final concentration 1 µM). The concentration of product was determined as described above.

All measurements were performed in at least duplicates and the inhibition constants ($K_i$) were determined by the equation below wherein $V_o$ and $V_i$ are activity in the absence and presence of inhibitors, respectively.

$$V_o/V_i = 1 + [I]/K_1$$

Assays were performed in HBSP buffer with either 1.5 nM CPM or 10 nM CPN with various concentrations of inhibitor in PEG-20,000 pre-coated 96-well microtiter plates. Enzymatic reactions continued for either 10 min (CPM) or 30 minutes (CPN) at room temperature. To an assay solution (150 µL) of enzyme and inhibitors was added 50 µL of 2 mM FA-AR and the rates of substrate hydrolysis were monitored by decrease of absorbance at 340 nm over 60 minutes using a Spectra 250 plate-reader (Molecular Device, Sunnyvale, Calif.).

Substituting other amino acids at the C-terminus expands application of the antibody recognition assay to other carboxypeptidases. Various detection methods may be used with this inventive assay to detect antibody binding. A HTRF assay could be used by replacing the labeled Ruthenium with Europium in G2-10 antibody coupled with streptavidin-coated fluorescence donor beads for energy transfer. Rogers, M. V. (1997) *Drug Discovery Today* 2, 156–160. Also, the AlphaScreen assay, with streptavidin-coated donor beads, unlabeled G2-10, and anti-mouse antibody-coated acceptor beads, was used to detect binding. Beaudet, L., Bedard, J., Breton, B., Mercuri, R. J. and Budarf, M. L. (2001), *Genome Res.* 11, 600–608. Results with the AlphaScreen format are discussed in Example 4.

EXAMPLE 4

AlphaScreen Assay for Basic Carboxypeptidase

Reactions were performed in a similar manner as the electrochemiluminescence assay in 96-well, flat-bottom, white Optiplates (Packard 6005190). Human TAFIa and CPB (10–200 pM) were incubated with inhibitor (6.7% DMSO in 75 µL reaction volume) for 30 min at room temperature. The reactions were initiated by the addition of the biotinylated electrochemiluminescence substrate (final concentration 50 nM), shaken briefly, and quenched after 30 min at room temperature with 25 µL of potato carboxypeptidase inhibitor (final concentration 800 nM). Unlabeled G210 antibody (final concentration 0.125 µg/mL), acceptor and donor beads (BioSignal Packard AlphaScreen Mouse IgG Detection kit; 6760606C, final concentration 10 µg/mL) were added for the final volume of 150 µL. All reagents were diluted with HBSP. The reactions were incubated ~15–20 hrs in complete darkness. Detection of emitted light at 520–620 nm was measured using an AlphaScreen Instrument (Packard model Fusion™ α-FP HT).

EXAMPLE 5

Electrochemiluminescence Assay for Inhibitors of Basic Carboxypeptidase

Several commercial inhibitors were tested with the electrochemiluminescence assay. Potato carboxypeptidase inhibitor-affinity-purified TAFIa and TAFIa that was partially isolated with Con-A chromatography was used to conduct the inhibition studies. TAFIa purified in its activated form from serum showed similar inhibitory potency to the TAFIa activated from zymogen for all inhibitors in the present study. Potato carboxypeptidase inhibitor is a widely studied peptide inhibitor for subfamily A carboxypeptidases. TAFIa and CPB were inhibited with identical affinity by potato carboxypeptidase inhibitor. Steady-state kinetics demonstrated that potato carboxypeptidase inhibitor is a competitive inhibitor of TAFIa and CPB. The chromogenic substrate, hippuryl-arginine, confirmed that potato carboxypeptidase inhibitor is a competitive inhibitor of TAFIa and CPB. For all subfamily B carboxypeptidases that were studied, potato carboxypeptidase inhibitor showed no inhibition at 50 µM. The selectivity of potato carboxypeptidase inhibitor for TAFIa makes this inhibitor a valuable tool to study the physiological effect of TAFIa distinguished from other regulatory enzymes. Small inhibitors such Plummer's Inhibitor and GEMSA showed some selectivity between TAFIa and its highly homologous counterpart, CPB. The inhibitory potency of both inhibitors toward CPB was two to three orders of magnitude greater than TAFIa. These results demonstrate that selective small molecular-weight inhibitors of TAFIa are possible. Both inhibitors also exhibited selectivity among the regulatory carboxypeptidases. Plummer's Inhibitor is a potent inhibitor for CPM ($K_i$ 3 nM) but exhibited much weaker inhibition for CPE ($K_i$ 710 nM). In contrast, GEMSA was a potent inhibitor for CPE ($K_i$ 16 nM) and 440-fold less potent for CPZ ($K_i$ 7 µM). The simple amino acid, ε-aminocaproic acid, was the weakest inhibitor for most carboxypeptidases (Ki≧1 mM) except CPE with a Ki of 8.2 µM, two orders of magnitude more potent than for the other enzymes. ε-aminocaproic acid and protamine are important compounds for clinical application. CPN is the only enzyme studied that was inhibited by protamine with a $K_i$ of 0.97 µM, similar to a previous report. Tang F., Jackman, H., Skidgel, R. A., Zsigmond, E. K., and Erdos, E. G. (1989), *Anesthesiology* 70, 267–275.

Inhibition constants for inhibition of human basic carboxypeptidase were determined at room temperature (TAFIa, CPB, CPM, and CPN) or at 37° C. (CPE and CPZ). Hydrolysis of substrate was measured in HBSP (pH 7.4) for TAFIa, CPB, CPM, and CPM. Activities of CPE and CPZ were measures in acetate buffer (pH 5.5) and Tris buffer (pH 7.4), respectively.

It will be apparent to those skilled in the art that various modifications and variations can be made to the method of purifying stable TAFIa and assays for detecting carboxypeptidase activity and inhibition without departing from the scope of the invention. The present invention include modifications and variations that are within the scope of the claims and their equivalents.

What is claimed is:

1. A process for purifying TAFIa from a serum sample comprising the sequential steps of a) adding a reversible inhibitor of TAFIa to the serum sample to form a first mixture; b) adding a coagulation initiator to the first mixture to convert TAFI to TAFIa and form a second mixture; c) applying the second mixture to a heparin-sepharose column to bind TAFI and TAFIa to the column; d) washing the heparin-sepharose column to remove proteins not bound to the heparin-sepharose column; e) eluting the bound TAFI and bound TAFIa from the heparin-sepharose column to form a third mixture; f) applying the third mixture to a TAFIa isolation column to bind TAFIa to the isolation column; g) washing the TAFIa isolation column to remove proteins not bound to the TAFIa isolation column; and h) eluting the bound TAFIa from the TAFIa isolation column.

2. The method of claim 1 wherein the reversible inhibitor is ε-aminocaproic acid, 2-mercaptomethyl-3-guanidinoethyl-propanoic acid, potato tuber carboxypeptidase inhibitor, leech carboxypeptidase inhibitor, or tomato carboxypeptidase inhibitor.

3. The method of claim 1 wherein the TAFIa isolation column is a potato carboxypeptidase inhibitor affinity column or a Con-A column.

4. The method of claim 1 wherein the coagulation initiator is selected from the group consisting of calcium chloride, thrombomodulin, or thrombin.

5. The method of claim 2 wherein the reversible inhibitor is ϵ-aminocaproic acid.

6. A method of measuring the activity of TAFIa in the presence of a reversible inhibitor comprising the sequential steps of: a) contacting a peptide, comprising a C-terminal carboxylate moiety masked by an amino acid, with TAFIa, in the presence of a reversible inhibitor of TAFIa, to form a first mixture; b) unmasking the C-terminal carboxylate moiety by hydrolyzing the amino acid with TAFIa; c) adding a labeled antibody or other labeled protein, which recognizes the unmasked C-terminal carboxylate moiety on the peptide, to the first mixture, to form a second mixture; and d) measuring the extent of hydrolysis by determining the amount of labeled antibody or other labeled protein bound to the unmasked C-terminal carboxylate moiety on the peptide of the second mixture.

7. The method of claim 6 wherein the reversible inhibitor is selected from the group consisting of ϵ-aminocaproic acid, 2-mercaptomethyl-3-guanidinoethyl-propanoic acid, potato tuber carboxypeptidase inhibitor, leech carboxypeptidase inhibitor, or tomato carboxypeptidase inhibitor.

8. The method of claim 6 wherein the peptide includes an N-terminal biotin.

9. The method of claim 7 wherein said reversible inhibitor is ϵ-aminocaproic acid.

* * * * *